United States Patent [19]

Polakowska et al.

[11] Patent Number: 5,643,746
[45] Date of Patent: Jul. 1, 1997

[54] HUMAN EPIDERMAL GENE PROMOTER

[75] Inventors: Renata Regina Polakowska; Lowell Alan Goldsmith, both of Pittsford, N.Y.

[73] Assignee: Research Corporation Technologies, Inc., Tucson, Ariz.

[21] Appl. No.: 216,219

[22] Filed: Mar. 21, 1994

Related U.S. Application Data

[63] Continuation of Ser. No. 73,190, Jun. 8, 1993, abandoned, which is a continuation of Ser. No. 826,931, Jan. 23, 1992, abandoned.

[51] Int. Cl.$^6$ .......................... C12N 15/63; C12N 15/79; C12N 15/09
[52] U.S. Cl. .................. 435/69.1; 435/320.1; 435/366; 435/371; 435/372.3; 935/62; 935/34; 935/70; 536/23.1
[58] Field of Search .................. 536/23.1; 435/320.1, 435/240.2, 172.3; 935/22, 70

[56] References Cited

U.S. PATENT DOCUMENTS 4,888,291  12/1989  Barrandon et al. .............. 435/240.241

OTHER PUBLICATIONS

Floyd, et al. (1989) *Mol. Cell. Biol.* 9:4846–4851, Regulation of Type I (Epidermal) Transglutaminase mRNA Levels During Squamous Differentiation: Down Regulation by Retinoids.
Gentile, et al. (1989) *J. Cell. Biol.* 109:198A, Isolation and Characterization of cDNA and Genomic Clones of Human Endothelial Cell Tranglutaminase.
Goldsmith, et al. (1991) *J. Invest. Dermatol.* 97: 156–158, Inhibition of Human Epidermal Transglutaminases In Vitro and In Vitro by Tyrosinamidomethyl Dihydrohaloisoxazoles.
Haake, et al. (1991) *J. Invest. Dermatol.* 96:71–77, Physiologic Distribution and Differentiation of Melanocytes in Human Fetal and Neonatal Skin Equivalents.
Ichinose, et al. (1988) *Proc. Natl. Acad. Sci. USA* 85:5829–5833,Characterization of the Gene for a Subunit of Human Factor XIII (plasma transglutaminase), a Blood Coagulation Factor.
Jetten, A.M. (1991) International Publication No. WO91/06553; PCT Appln. No. PCT/US90/067075, Type I Transglutaminase DNA, published May 16, 1991, claiming priority of U.S. Serial No. 425887, filed Oct. 24, 1989.
Kim, et al. (1991) *J. Biol. Chem.* 226:536–539,The Complete Amino Acid Sequence of the Human Transglutaminase K Enzyme Deduced from the Nucleic Acid Sequences of cDNA Clones.
Michel, et al. (1989) *FEBS Lett.* 258:35–38, Retinoic Acid Controls Expression of Epidermal Translutaminase at the Pre-translational Level.

Phillips, et al. (1990) *Proc. Natl. Acad. Sci. USA* 87:9333–9337, Primary Structure of Keratinocyte Transglutaminase.
Polakowska, et al. (1991) *J. Invest. Dermatol.* 96:285–288, Isolation of cDNA cDNA for Human Epidermal Type I Transglutaminase.
Polakowska, et al. (1990) *J. Invest. Dermatol.* 94:567, Cloning of Human Epidermal type I Transgutaminase (TGase).
Schroeder, et al. (1990) *Clin. Res.* 38:962A, Isolation of a cDNA for Human Epidermal Transglutaminase (Type I).
Yamanishi, et al. (1991) *Biochem. Biophys. Res. Comm.* 175: 906–913, Molecular Cloning of Human Epidermal Transglutaminase cDNA from Keratinocytes in Culture.
Wolff et al. (1990) *Science* 247:1465–1468, Direct Gene Transfer into Mouse Muscle in Vivo.
Morgan et al. (1990) *Science* 247:1465–1468, Direct Gene Transfer into Mouse Muscle in Vivo.
St. Louis et al. (1988) *Proc. Natl. Acad. Sci.* 85:3150–3154 An Alternative Approach to Somatic Cell Gene Therapy.
Fenjves et al. (1989) *Proc. Natl. Acad. Sci.* 86:8803–8807, Systemic Distribution of Apolipoprotein E Secreted by Grafts of Epidermal Keratinocytes: Implications for Epidermal Function.
Fenjves et al. (1990) *DNA Damage and Repair in Human Tissues*, Sutherland et al., eds., Plenum Press, New York pp 215–223.
Jensen et al. (1991) *J. Cell Sci.* 100:255–259, Tissue Culture of Human Epidermal Keratinocytes:a Differentiating Model System for Gene Testing and Somatic Gene Therapy.
Miller (1990) *Blood* 76:271–278, Progress Toward Human Gene Therapy.
International search Report PCT/US 93/00537.
Phillips et al. (1992) *J. Biol. Chem.* 267:2282–2286, Genomic Structure of Keratinocyte Transglutaminase.
Kim et al. (1992) *J. Biol. Chem.* 267:7710–7717, Structure and Organization of the Human Transglutaminase 1 Gene.
Yamanashi et al. (1992) *J. Biol. Chem.* 267:17858–17863, Structure of the Gene for Human Transglutaminase 1.

*Primary Examiner*—Jasemine C. Chambers
*Assistant Examiner*—Karen M. Hauda
*Attorney, Agent, or Firm*—Scully, Scott, Murphy & Presser

[57] ABSTRACT

The present invention relates to promoter elements from human type I transglutaminase (TGase I) genes for controlled gene expression of both human TGase I and heterologous proteins. These promoter elements permit tissue-specific expression of genes, e.g. for use in human gene therapy and for testing pharmaceutical agents with artificial skin. Additionally, the subject promoter elements can provide differential regulation under physiological conditions or in the presence of exogenously added factors including calcium and retinoic acid.

17 Claims, 5 Drawing Sheets

HUMAN EPIDERMAL GENE PROMOTER

This is a continuation of application Ser. No. 08/073,190, filed on Jun. 8, 1993, now abandoned which is a Rule 60 continuation of Ser. No. 07/826,931 filed on Jan. 23, 1992, now abandoned.

This invention was made with Government support under Grant Nos. 2-R01-AR-30965-10 and R29-AR-39724 awarded by the National Institutes of Health. The Government has certain rights in the invention.

FIELD OF THE INVENTION

The present invention relates to promoter elements from the human type I transglutaminase (TGase I) gene for controlled gene expression of both human TGase I and heterologous proteins. These promoter elements permit tissue-specific expression of genes, e.g. for use in human gene therapy and for testing pharmaceutical agents with skin equivalents. Additionally, the subject promoter elements can provide differential regulation under physiological conditions or in the presence of exogenously added factors including calcium and retinoic acid.

BACKGROUND OF THE INVENTION

Transglutaminases are calcium-dependent enzymes which catalyze acyl transfer reactions that lead to the amination of proteins with small primary amines or the crosslinking of proteins by the formation of $\epsilon(\gamma$-glutamyl) lysine transpeptide bonds. This crosslinking activity typically results in the covalent joining of soluble proteins into large chemically, enzymatically and mechanically resistant polymers with diverse biological functions.

Several classes of transglutaminase exist and form a family of genes. The "a" subunit of factor XIII (XIIIa) participates in blood clot formation by crosslinking fibrin. Factor XIIIa is a soluble protein in the plasma and in placenta; it is also know as plasma TGase. TGase I is a differentiation marker for keratinocytes and plays a role in formation of the cornifying envelope in epidermal keratinocytes. TGase I is predominantly membrane-bound, and has been variously identified in the literature as particulate TGase, epidermal TGase, and TGase K. TGase II is ubiquitously distributed in the cytosol. The physiological role of TGase II is not well understood. This enzyme is also known as tissue TGase, liver TGase, intracellular TGase, soluble TGase and TGase C. Band 4.2 protein also belongs to the TGase gene family although this protein lacks transglutaminase activity.

TGase I gene expression appears to be limited to the terminally differentiating keratinocyte in vivo and in vitro. In these cells, the formation of an insoluble protective structure, the cell envelope, just beneath the plasma membrane is associated with increased crosslinking activity of TGase, which in turn is correlated with an increased level of TGase I mRNA [Polakowska et al. (1991) *J. Invest. Dermat.* 96:285–288]. TGase I expression, as well as terminal differentiation, are regulated by several environmental factors of which $Ca^{2+}$ and retinoic acid (RA) appear to have the most profound effect. Hence, TGase I provides a convenient marker for keratinocyte differentiation.

A cDNA clone for the human TGase I gene, and the sequence thereof has been reported by several investigators [Kim et al. (1991) *J. Biol. Chem.* 266:536; Phillips et al. (1990) *Proc. Natl. Acad. Sci. USA* 87:9333; Polakowska et al. (1990) *J. Invest. Dermat.* 94:567; Polakowska et al. (1991) *J. Invest. Dermat.* 96:285; Schroeder et al. (1990) *Clin. Res.* 38:962A; Yamanishi et al. (1991) *Biochem. Biophys. Res. Comm.* 175:906]. However, the genomic gene for human TGase I with its concomitant regulatory regions has heretofore been unavailable and therefore uncharacterized.

The present invention arose from the identification and characterization of the human TGase I genomic DNA. Accordingly, once the human genomic DNA was available, the regulatory regions, or elements, responsible for initiating and controlling transcription of human TGase I were elucidated as provided by the present invention. Since TGase I is expressed in a tissue-specific manner, i.e. in terminally differentiating keratinocytes, the subject regulatory regions are particularly useful in construction of tissue-specific expression vectors as well as to provide promoter elements responsive to calcium and retinoic acid. Moreover, each of the regulatory elements of the present invention is useful in combination with known promoter or regulatory elements. These combinations enable modification of the host-cell or condition responsiveness of other vectors and thus provide additional means to control gene expression. Such combinations provide greater flexibility in selecting vectors to control expression in a selected cell type or under a particular set of conditions.

By identifying and characterizing the human TGase I promoter elements and linking these elements to marker genes, other factors which may regulate expression, such as pharmaceutical and cosmetic agents for the skin, can be examined. Further, using the promoter regulatory elements identified by the present invention, expression vectors can be constructed which direct expression of heterologous gene products in skin equivalents or which direct altered expression of TGase in skin equivalents. Skin equivalents, or artificial skin, are epidermal cells grown in tissue culture which have many uses including skin grafts, especially for burn victims, and testing pharmaceutical and cosmetic products as well as the individual constituents of such products.

Hence, the present invention provides expression vectors containing the transcriptional regulatory region(s), (i.e. elements of the promoter region) of the human TGase I gene which are particularly useful for human gene therapy to treat diseases of the epidermis or to deliver drugs in a cell-specific manner, for production of skin equivalents, and for the use with skin equivalents to provide in vitro testing of pharmaceutical and cosmetic products.

SUMMARY OF THE INVENTION

The present invention is directed to the transcriptional regulatory regions from the human type I transglutaminase (TGase I) gene. These regulatory regions can control tissue-specific expression of any gene coupled thereto in either a positive or negative manner depending on the element which is present. More particularly, these regions include at least one keratinocyte-specific regulatory element, at least one calcium-responding regulatory element and/or at least one retinoic acid-responding regulatory element and are located in the DNA extending upstream to about 2 kilobase pairs (kb) from the 5' end of the second exon contained in the genomic human TGase I gene.

Another aspect of the present invention provides replicable expression vectors having the subject regulatory regions operably linked to the DNA encoding a gene product and host cells containing such vectors. These gene products can be TGase I, keratinocyte-specific genes such as keratins, marker genes, or another heterologous gene product.

In a further aspect this invention provides a method for keratinocyte-specific expression of a gene product by cultivating a keratinocyte cell containing one of the subject expression vectors for a time and under conditions sufficient to express the gene product under control of the keratinocyte-specific regulatory element. Such a method can be practiced, with the appropriate controls, for testing the effects of pharmaceutical and cosmetic products on the expression of marker genes in artificial skin (skin equivalents), e.g. the keratinocytes.

Yet another aspect of the instant invention provides a method of human gene therapy for treating epidermal diseases or drug delivery by administering to a human an expression vector capable of effecting tissue-specific expression of a gene product in a therapeutic amount, wherein said expression vector has a transcriptional regulatory region from a human type I transglutaminase gene operably linked to the DNA encoding the gene product.

A still further aspect of the present invention provides a method of human gene therapy for treating epidermal diseases or delivering drugs to the epidermis by transforming human skin equivalents with one of the subject expression vectors, culturing the transformed skin equivalents for a time and under conditions effective to produce sufficient skin equivalents to apply to a patient, applying the mass of transformed skin equivalents to the patient and inducing expression of the gene product, as necessary, to thereby deliver the drug or effect the desired epidermal therapy.

DETAILED DESCRIPTION OF THE INVENTION

Figure 1:
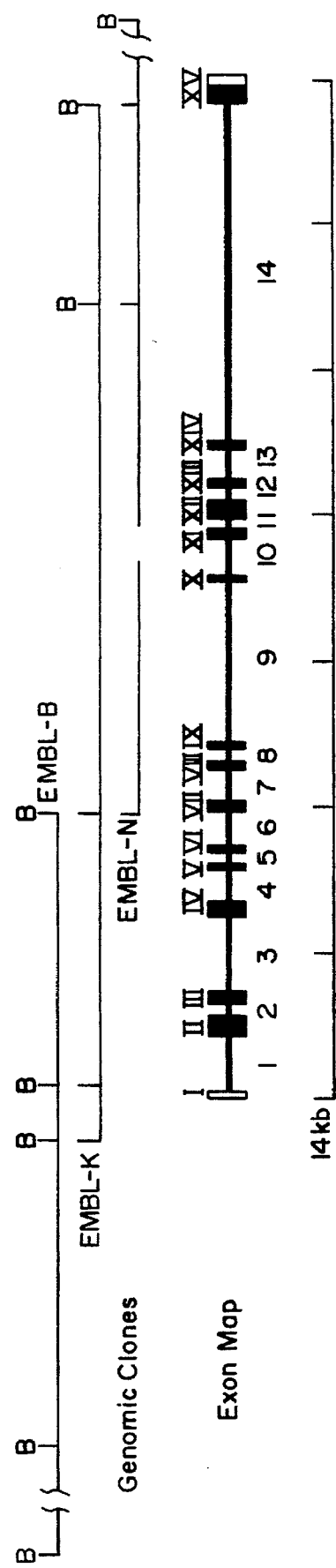
FIG. 1 illustrates the relationship between three genomic clones EMBL-B, EMBL-K, EMBL-N, and the genomic organization of the human TGase I gene which contains 15 exons and 14 introns. Top thin lines provide a BamHI restriction map of the three clones. The Exon Map (center) shows the distribution of introns (thick lines; arabic numerals) and exons (boxes; roman numerals). The 5'- and 3'- untranslated regions are indicated by open boxes.

The present invention is directed to the transcriptional regulatory regions from the human type I transglutaminase (TGase I) gene. These regulatory regions, or promoter elements, can control tissue-specific expression of any coding sequence coupled thereto. Moreover, expression can be controlled in either a positive or negative manner depending on the selection of promoter elements. More particularly, these promoter elements include at least one keratinocyte-specific regulatory element, at least one calcium (Ca)-responding regulatory element and/or at least one retinoic acid (RA)-responding regulatory element and are located in the DNA extending upstream to about 2 kilobase pairs (kb) from the 5' end of the second exon of the genomic human TGase I gene.

The general techniques used for the subject invention, especially in preparing and probing a genomic library, sequencing clones, performing deletion analysis, constructing expression vectors, transforming cells, for growing cells in culture, and the like are known in the art and laboratory manuals are available describing these techniques. Hence, the present invention employs, unless otherwise indicated, conventional techniques of molecular biology, microbiology, cell culture and recombinant DNA which are with the skill of the art. Examples of useful laboratory manuals include Sambrook et al. (1989) *Molecular Cloning: A Laboratory Manual*, 2nd Ed., Cold Spring Harbor Laboratory Press, Cold Spring Harbor, N.Y.; and Miller et al. (1987) *Gene Transfer Vectors for Mammalian Cells*, Cold Spring Harbor Laboratory Press, Cold Spring Harbor, N.Y.

The following general definitions apply to the present invention. More specific definitions for various aspects of the present invention are also provided herein.

The term "polynucleotide" or "nucleic acid" as used herein refers to a polymeric form of nucleotides of any length, either ribonucleotides or deoxyribonucleotides. This term refers only to the primary structure of the molecule. Thus, this term includes double- and single-stranded DNA, as well as double- and single-stranded RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.) those with intercalators (e.g., acridine, psoralen, etc.), those containing chelators (e.g., metals, radioactive metals, boron, oxidative metals, etc.) those containing alkylators, those with modified linkages (e.g., alpha anomeric nucleic acids, etc.), as well as unmodified forms of the polynucleotide.

As used herein, a polynucleotide "derived from" a designated sequence refers to a polynucleotide sequence which is comprised of a sequence of approximately at least about 6 nucleotides, preferably at least about 8 nucleotides, more preferably at least about 10–12 nucleotides, and even more preferably at least about 15–20 nucleotides corresponding to a region of the designated nucleotide sequence. "Corresponding" means homologous to or complementary to the designated sequence. Preferably, the sequence of the region from which the polynucleotide is derived is homologous to or complementary to a sequence which is unique to a human TGase I gene. Whether or not a sequence is unique to a human TGase I gene can be determined by techniques known to those of skill in the art. For example, the sequence can be compared to sequences in databanks, e.g., Genebank, to determine the uniqueness and relatedness to known sequences using conventional computer programs. The correspondence or non-correspondence of the derived sequence to other sequences can also be determined by hybridization under the appropriate stringency conditions. Hybridization techniques for determining the complementarity of nucleic acid sequences are known in the art. See also, for example, Sambrook et al. (1989). In addition, mismatches of duplex polynucleotides formed by hybridization can be determined by known techniques, including for example, digestion with a nuclease such as S1 that specifically digests single-stranded areas in duplex polynucleotides. Regions from which typical DNA sequences may be "derived" include but are not limited to, for example, regions encoding specific regulatory elements, as well as non-transcribed and/or non-translated regions.

The derived polynucleotide is not necessarily physically derived from the nucleotide sequence shown, but may be generated in any manner, including for example, chemical synthesis or DNA replication or reverse transcription or transcription. In addition, combinations of regions corresponding to that of the designated sequence may be modified in ways known in the art to be consistent with an intended use.

The term "recombinant nucleic acid" as used herein means a nucleic acid of genomic, semisynthetic, or synthetic origin which, by virtue of its origin or manipulation which: (1) is not associated with all or a portion of a polynucleotide with which it is associated in nature, (2) is linked to a polynucleotide other than that to which it is linked in nature, or (3) does not occur in nature.

"Recombinant host cells", "host cells", "cells", "cell lines", "cell cultures", and other such terms denoting microorganisms or higher eukaryotic cell lines cultured as unicellular entities refer to cells which can be, or have been, used as recipients for recombinant expression vectors or other transfer DNA, and include the progeny of the original cell which has been transfected. It is understood that the progeny of a single parental cell is not necessarily completely identical in morphology or in genomic or total DNA complement as the original parent, due to natural, accidental, or deliberate mutation.

"Control sequence", "regulatory element", and "regulatory region" refer to polynucleotide or nucleic acid sequences which are necessary to effect the expression of the coding sequences of the gene products to which they are operably joined. The nature of such control sequences differs depending upon the host organism; in eukaryotes, generally, such control sequences include promoters, terminators and, in many instances, enhancers. The term "control sequences" is intended to include, at a minimum, all components whose presence is necessary for expression, and may also include additional components whose presence is advantageous, for example, leader sequences, and other regulatory sequences such as the sequences which provide keratinocyte-specific expression, calcium-responding ability and retinoic acid-responding ability of the subject regulatory elements of the present invention.

"Operably linked" refers to a juxtaposition of sequence elements, regulatory elements, control sequences and the like with coding sequences for a gene product, wherein the components so described are joined one to another in a relationship permitting them to function in their intended manner. A control sequence "operably linked" to a coding sequence is ligated in such a way that expression of the coding sequence is achieved under conditions compatible with the control sequences. In particular, the subject regulatory elements, as many as are necessary or desired, are typically joined to the coding sequence of a gene product to achieve controlled expression of that gene product consistent with the function (capability) of selected regulatory elements.

A "coding sequence" is a polynucleotide sequence which is transcribed into mRNA and/or translated into a polypeptide when placed under the control of appropriate regulatory sequences. A coding sequence encodes a gene product. The boundaries of the coding sequence are determined by a translation start codon at the 5'-terminus and a translation stop codon at the 3'-terminus. A coding sequence can include, but is not limited to mRNA, cDNA, and recombinant polynucleotide sequences and can, optionally, include introns.

"Transformation", as used herein, refers to the insertion of an exogenous polynucleotide or recombinant nucleic acid into a host cell, irrespective of the method used for the insertion, for example, direct uptake, lipid-mediated transfection, transfection, transduction, f-mating or electroporation. The exogenous polynucleotide may be maintained as a non-integrated vector, for example, a plasmid, or alternatively, may be integrated into the host genome.

As used herein, the term "probe" refers to a polynucleotide which forms a hybrid structure with a sequence in a target region of a nucleic acid, due to complementarity of at least one sequence in the probe with a sequence in the target region.

Accordingly, the present invention is directed to the transcriptional regulatory elements from the promoter region of the human TGase I gene. These elements have been identified and characterized from a genomic clone of the human TGase I gene. To obtain a genomic clone, a human genomic library can be screened using an oligonucleotide probe derived from the cDNA sequence of human TGase I or the genomic sequence provided by the present invention. The cDNA sequences are provided, for example, by Polakowska et al. (1991) and others as set forth in the "Background". Human genomic DNA libraries can be obtained commercially or constructed using standard methodology. DNA libraries can be probed using any of several procedures provided by Sambrook et al.

A restriction map of the genomic gene for human TGase I is provided in FIG. 1. This figure illustrates the intron-exon structure of the human TGase I gene, which contains 14 introns and 15 exons spanning an approximately 14 kb region. The transcriptional regulatory region, i.e., the promoter region of the human TGase I gene as provided by this invention resides at the 5' end of this gene and includes sequences located 5' to the transcription initiation site (up to about 930 bp of sequence), the TATA box, the transcription initiation site (the CAP site), the 5'-untranslated region with the first exon, and the first intron. The sequence of this promoter region and part of Exon II are provided in SEQ ID NO:1. Table 1 identifies various features in the human TGase I promoter region as well as selected restriction sites.

TABLE I

Selected Features of the Human TGase I
Promoter Region Represented in SEQ ID NO: 1

| Feature | Nucleotide |
| --- | --- |
| TATA box | 901–905 |
| Exon I | 936–1021 |
| Intron 1 | 1022–1955 |
| Exon II | 1756–end[a] |
| BamHI sites | 485 and 1088 |
| HindIII sites | 616 and 1569 |
| NlaIII sites | 1563 and 1757[b] |
| AUG initiation codon | 1758 |

[a]The full sequence of exon II is not provided.
[b]Only the pertinent NlaIII sites are identified.

The human TGase I promoter region is provided by nucleotides 1–1757 of SEQ ID NO:1. This fragment contains at least one keratinocyte-specific regulatory element, at least one Ca-responding regulatory element and at least one RA-responding regulatory element. The keratinocyte-specific regulatory element has been identified on the basis that this fragment, the BamHI fragment and the NlaIII-194 fragment exhibit lower promoter activity in fibroblasts as compared to keratinocytes.

The BamHI fragment (nucleotides 485–1093 of SEQ ID NO:1) contains at least one keratinocyte-specific regulatory element and one Ca-responding regulatory element. This Ca-responding regulatory element provides positive regulation of gene expression in the presence of high calcium ($Ca^{2+}$). High $Ca^{2+}$ as used herein is greater than or equal to 0.5 mM $Ca^{2+}$, and preferably greater than or equal to 1.0 mM $Ca^{2+}$. Thus, high $Ca^{2+}$ can range from about 0.5 mM to about 5 mM. Even more preferably, high $Ca^{2+}$ is about 1.2 mM.

The HindIII fragment (nucleotides 616 to 1574 of SEQ ID NO:1) contains a negative regulatory element which inhibits calcium and retinoic acid responsiveness.

The NlaIII-194 fragment (nucleotides 1563 to 1760 of SEQ ID NO:1) contains at least one keratinocyte-specific regulatory element, at least one Ca-responding regulatory element, and at least one RA-responding regulatory element. Retinoic acid levels capable of controlling gene expression range from about $10^{-7}$M to about $10^{-5}$M, and preferably are about $10^{-6}$M. These two Ca- and RA-responding regulatory elements are capable of negative regulation of gene expression. For $Ca^{2+}$, such negative regulation is manifest in the presence of high $Ca^{2+}$ as defined hereinbefore.

As used herein, "keratinocyte-specific regulatory element" refers to a polynucleotide sequence that is capable of causing the expression of the gene product under its control to occur in keratinocyte cells. For example, keratinocyte-specific regulatory elements do not direct expression in fibroblasts. The gene product is present in keratinocytes when expression is initiated and the keratinocyte-specific regulatory element is controlling such expression in a positive manner. When the keratinocyte-specific regulatory element is controlling expression in a negative manner, the gene product is either absent from keratinocytes, or the levels of the gene product are reduced.

Keratinocytes are one of several skin cells, i.e. cells which are capable of producing epidermis. As used herein "keratinocytes" are any proliferating and/or differentiating epidermal cells, including primary cultures of fetal skin keratinocytes, neonatal skin keratinocytes and adult keratinocytes. Moreover, as used herein "keratinocytes" include keratinocyte-like cells which are epithelial keratinocytes with further specialized differentiation properties but which express the characteristic keratinocyte genes, especially the keratin genes and transglutaminase. Epithelial keratinocytes are the keratinocyte-like cells of specialized epithelia which include pharnyx, oropharnyx, mouth, tongue, trachea, bronchial epithelia, conjunctiva, cornea, vagina, cervix, and further include both normal and malignant keratinocyte-like cells from these specialized epithelia. Further, "keratinocytes" include epidermal cells capable of sustained growth in tissue culture (i.e. established cultured cells) including neoplastic or transformed epidermal cells. A primary cell line includes cells which have been passaged in culture from one to several times before either dying or undergoing transformation to an established cultured cell line.

To identify regulatory elements that direct keratinocyte-specific expression, deletion analysis of the human TGase I promoter region is performed. Deletion analysis involves constructing vectors having polynucleotide sequences, i.e. portions of the promoter region, operably linked to a marker gene. These vectors are then assayed for the ability to direct expression of the marker gene in keratinocytes but not in other cell types such as fibroblasts. In this manner, polynucleotide sequences of the promoter region are examined to identify keratinocyte-specific regulatory elements. These polynucleotide sequences are from the human TGase I promoter region and can be composed of restriction fragments, synthetic oligonucleotides, fragments generated by enzymatic digestion with exonucleases such as Bal31, any combination of these fragments, or any fragment of the human TGase I promoter region available by conventional means in the art. Similarly, once a keratinocyte-specific regulatory element has been identified and characterized, these elements can be modified by substituting, inserting, deleting or inverting nucleotides to identify alternative polynucleotide sequences which also confer keratinocyte-specific expression. These modified regulatory elements can be made conveniently by site-specific mutagenesis, by deletion using Bal31 or other conventional means, and then assayed for keratinocyte-specific expression using a marker gene.

Marker genes include the CAT gene, β-glucuronidase (GUS), β-galactosidase (β-gal) and the like. Such genes are assayed by conventional means known in the art including enzymatic activity, histochemical localization, immunoassay, colorimetric assay, and fluorescence. The assays can be conducted on a quantitative or qualitative basis to evaluate keratinocyte-specific expression.

Keratinocyte-specific regulatory elements of the present invention are present in the human TGase I promoter region provided by nucleotides 1–1757 of SEQ ID NO:1, by the BamHI fragment provided by nucleotides 485–1093 of SEQ ID NO:1 and by the NlaIII-194 fragment provided by nucleotides 1563 to 1760 of SEQ ID NO:1.

As used herein, "Ca-responding regulatory element" refers to a polynucleotide sequence that is capable of causing the expression of the gene product under its control to respond to high calcium. The responsiveness to high calcium can effect either positive or negative regulation of the gene product. When control occurs in a positive manner, the presence of high calcium stimulates gene expression. When control occurs in a negative manner, the presence of high calcium inhibits gene expression.

To identify Ca-responding regulatory elements, a deletion analysis of the human TGase I promoter region is performed in a manner similar to that described for identifying keratinocyte-specific regulatory elements. The analysis differs, however, in that the vectors are assayed for the ability to direct expression of the marker gene in response to high calcium. High calcium is as defined hereinbefore. Moreover, such assays are not necessarily limited to keratinocytes but can be conducted in any convenient cell type.

Ca-responding regulatory elements of the present invention are present in the human TGase I promoter region provided by nucleotides 1 to 1757 of SEQ ID NO:1. The BamHI fragment (nucleotides 485 to 1093 of SEQ ID NO:1) provides a Ca-responding regulatory element which confers positive regulation of gene expression. The HindIII fragment (nucleotides 616 to 1574) contains a negative regulatory element which overrides (i.e. is dominant to) the regulatory control of the NlaIII-194 fragment.

As used herein, "RA-responding regulatory element" refers to a polynucleotide sequence that is capable of causing the expression of the gene product under its control to respond to retinoic acid. The responsiveness to retinoic acid can produce either positive or negative regulation of the gene product. When control occurs in a positive manner, the presence of retinoic acid stimulates gene expression. When control occurs in a negative manner, the presence of retinoic acid inhibits gene expression. Similarly, the response to retinoic acid can be examined in the presence of high calcium and, under some conditions, occurs only in the presence of high calcium, i.e. the retinoic acid-responding regulatory element is only active (operable) in the presence of high calcium.

To identify RA-responding regulatory elements, a deletion analysis of the human TGase I promoter region is performed in a manner similar to that described for identifying keratinocyte-specific regulatory elements. The analysis differs however, in that the vectors are assayed for the ability to direct expression of the marker gene in response to retinoic acid. The amount of retinoic acid is as defined hereinbefore. Such assays are not necessarily limited to keratinocytes but can be conducted in any convenient cell type, as well as in the presence or absence of high calcium.

RA-responding regulatory elements of the present invention are present in the human TGase I promoter region provided by nucleotides 1 to 1757 of SEQ ID NO:1. The NlaIII-194 fragment (nucleotides 1563 to 1760 of SEQ ID NO:1) provides a RA-responding regulatory element which confers negative regulation of gene expression in the presence of high calcium. The HindIII fragment (nucleotides 616 to 1574) contains a negative regulatory element which eliminates (i.e. overrides) the regulatory control of the NlaIII-194 fragment.

Another aspect of the present invention provides replicable expression vectors having the subject regulatory regions and elements operably linked to the DNA encoding a gene product and host cells containing such vectors. These gene products can be human TGase I, human keratinocyte-specific genes such as keratins including acidic and basic keratins, marker genes, or any other heterologous gene product. Marker genes include CAT, GUS, β-gal and the like. Heterologous gene products are products encoded by foreign DNA (relative to the human TGase I gene) for which expression is desired under control of the regulatory elements of the present invention. Examples of heterologous gene products include proteins for treatment of epithelial or epidermal diseases, proteins which potentiate therapeutic effects as pharmacological agents, and the like. Such heterologous proteins individually or in combination include interferons (α, β or γ), interleukins (IL1–9) including IL-1α and IL-1β, colony stimulating factors (GM-CSF, G-CSF, M-CSF and IL-3), retinoic acid receptors (α, β, γ), steroid hormone receptors, vitamin D receptors, cystic fibrosis transmembrane receptor protein (CFTR), epidermalysin and the epidermal proteins keratins, filaggrin and loricrin. Likewise, the heterologous proteins can include enzymes which are capable of modifying a cellular constituent to produce a pharmaceutically active agent.

Vector construction employs techniques which are known in the art. Site-specific DNA cleavage is performed by treating DNA with suitable restriction enzymes under conditions which generally are specified by the manufacturer of these commercially available enzymes. In general, about 1 microgram of plasmid or DNA sequence is cleaved by 1 unit of enzyme in about 20 microliters buffer solution by incubation of 1–2 hr at 37° C. After incubation with the restriction enzyme, protein can be removed by phenol/chloroform extraction and the DNA recovered by precipitation with ethanol. The cleaved fragments can be separated using polyacrylamide or agarose gel electrophoresis techniques, according to the general procedures found, for example, in Methods of Enzymology (1980) 65:499–560.

Sticky-ended cleavage fragments can be converted to blunt-ended fragments using E. coli DNA polymerase 1 (Klenow) in the presence of the appropriate deoxynucleotide triphosphates (dNTPs) present in the mixture. Alternatively, treatment with S1 nuclease can also be used, resulting in the hydrolysis of any single-stranded DNA portions.

Ligations are carried out using standard buffer and temperature conditions with T4 DNA ligase and ATP; sticky-end ligations require less ATP and less ligase than blunt-end ligations. When vector fragments are used as part of a ligation mixture, the vector fragment is often treated with bacterial alkaline phosphatase (BAP) or calf intestinal alkaline phosphatase to remove the 5'-phosphate and thus prevent religation of the vector; alternatively, restriction enzyme digestion of unwanted fragments can be used to prevent ligation.

Ligation mixtures are transformed into suitable cloning hosts, such as E. coli, and successful transformants selected by, for example, antibiotic resistance, and screened for the correct construction.

Host cells include prokaryotic hosts (for vector construction and testing) and eukaryotic hosts (for vector construction and testing, for expression and treatment). Vectors are introduced by transformation into the appropriate host.

Transformation may be by any known method for introducing polynucleotides into a host cell, including, for example packaging the polynucleotide in a virus and transducing a host cell with the virus, and by direct uptake of the polynucleotide or vector. The transformation procedure used depends upon the host to be transformed. Bacterial transformation by direct uptake generally employs treatment with calcium or rubidium chloride. Yeast transformation can be by direct uptake. Mammalian transformations by direct uptake may be conducted using the calcium-phosphate precipitation method or the various known modifications thereof. Transformation methods are provided, for example, by Sambrook et al.

Prokaryotic hosts are preferably used during construction of the subject expression vectors whereas eukaryotic host cells are used for expression of desired gene products using regulatory sequences compatible with the designated host. Among prokaryotic hosts, E. coli is most frequently used. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection for antibiotic resistance.

Eukaryotic hosts include yeast and mammalian cells, including human epidermal cells, in culture systems. Saccharomyces cerevisiae and Saccharomyces carisbergensis are the most commonly used yeast hosts. Yeast compatible vectors carry markers which permit selection of successful transformants by conferring prototrophy to auxotrophic mutants or resistance to heavy metals on wild-type strains. Control sequences for yeast vectors are known in the art and include promoters for the synthesis of glycolytic enzymes, including the promoter for 3-phosphoglycerate kinase. Terminators can also be included, such as those derived from the enolase gene.

Mammalian cell lines available as hosts for expression are known in the art and include keratinocytes as defined hereinbefore as well as many immortalized cell lines available from the American Type Culture Collection (ATCC), including HeLa cells, Chinese Hamster ovary (CHO) cells, baby hamster kidney (BHK) cells, and a number of other cell lines. Suitable promoters for mammalian cells are also known in the art and include viral promoters such as that from Simian Virus 40 (SV40), Rous sarcoma virus (RSV), adenovirus (ADV), and bovine papilloma virus (BPV). Mammalian cells can also require terminator sequences and poly A addition sequences; enhancer sequences which increase expression may also be included, and sequences which cause amplification of the gene can be included if desirable. These sequences are known in the art. Vectors suitable for replication in mammalian cells may include viral replicons, or sequences which insure integration of the appropriate sequences into the host genome.

In a further aspect, the present invention provides a method for keratinocyte-specific expression of a gene product by cultivating a keratinocyte cell containing one of the expression vectors of this invention for a time and under conditions sufficient to express the gene product under control of the keratinocyte-specific regulatory element. For example, such a method can be practiced, with the appropriate controls, for testing the effects of pharmaceutical and cosmetic products on controlling expression, using marker genes in skin equivalents, i.e. keratinocytes.

In this embodiment, keratinocytes are transformed with an expression vector of the present invention. Such vectors contain at least one keratinocyte-specific regulatory element of the present invention, and can optionally contain one or more of the other regulatory elements of this invention. After selection for presence of the vector, the cell line containing that vector can be expanded to generate a sufficient number of keratinocytes from which to obtain expression as needed for the purpose at hand. These keratinocyte cells are then cultured under conditions to induce expression of the gene product. For example, if the vector contains a positive Ca-responding regulatory element, then the keratinocytes are cultured in growth medium with the addition of high calcium (e.g. 1.2 mM $Ca^{2+}$) until the gene product is expressed.

To test the effects of pharmaceutical and cosmetic products on human TGase I regulatory elements, expression vectors are constructed which have the desired regulatory elements operably linked to a marker gene. Keratinocyte cells or skin equivalents containing these vectors are then cultured under conditions which induce gene expression (conditions consistent with the regulatory element employed) but also in the presence of the pharmaceutical or cosmetic product under investigation.

As used herein, pharmaceutical and cosmetic products include complete formulations as well as the individual ingredients in these formulations. Preferred products include formulations, ingredients, agents and the like which have a therapeutic benefit or potential therapeutic benefit for the skin, epidermis or specialized epithelia. Similarly, this method can be used to screen any product to determine the potential effect, either beneficial or detrimental, of that product on the skin, epidermis or specialized epithelia.

Yet another aspect of the instant invention provides a method of human gene therapy for treating epithelial diseases, epidermal diseases or drug delivery by administering to a human an expression vector capable of effecting tissue-specific expression of a gene product in a therapeutic amount, wherein said expression vector has a transcriptional regulatory region of the present invention (from a human type I transglutaminase gene) operably linked to DNA encoding a gene product.

Epithelial diseases treatable in accordance with the present invention include cystic fibrosis.

Epidermal diseases treatable in accordance with the present invention include eczema, psoriasis, ichthyosis, pemphigus vulgaris and foliaceous, lamellar ichthyosis, epidermalytic hyperkeratosis, genetic and acquired diseases of the basement membrane zone (which is derived from the epidermis) including forms of epidermalysis bullosa and bullous pemphigoid.

For example, drugs which can be delivered by the methods of this invention include hormones produced in the skin equivalents including growth hormone, insulin, parathyroid hormone, ACTH, substance P, endogenous opiates and the like.

The expression vector can be administered directly to a human, or used to transform human cells which are then administered to a human. Accordingly, when the physiological conditions are appropriate, the gene products under control of the regulatory elements of the present invention are expressed. The physiological conditions can be manipulated if necessary by administering drugs to or by controlled diet of the human who receives the vector. When the vector is administered, directly or indirectly, to a human, the vector can be transferred into the cells of said human by a second nucleic acid, e.g. by a viral nucleic acid, or by another carrier, such as a virus or encapsidated in a viral coat protein or viral envelope.

A still further aspect of the present invention provides a method of human gene therapy for treating epithelial diseases, epidermal diseases or delivering drugs by transforming human skin equivalents with one of the subject expression vectors, culturing the transformed skin equivalents for a time and under conditions effective to produce sufficient skin equivalents to apply to a patient, applying the mass of transformed skin equivalents to the patient and inducing expression of the gene product, as necessary, to thereby deliver the drug or effect the desired therapy.

Skin equivalents or artificial skin are an epithelial sheet produced from human keratinocytes including the keratinocyte-like cells of specialized epithelia according to conventional means known in the art, for example, as provided in Haake et al. (1991) *J. Invest. Dermat.* 96:71–77 or U.S. Pat. No. 4,888,291 which are incorporated herein by reference. Skin equivalents can be transformed at any stage during formation of the epithelial sheet that makes up the skin equivalents, preferably the human keratinocytes are transformed before sheet formation occurs.

In some instances expression of the gene product in the transformed cells is accomplished before the transformed skin equivalents are applied to the patient. Hence, the growth media for the skin equivalents is supplemented with the agents necessary to induce gene expression using the subject expression vectors. In other instances expression of the gene product is accomplished after the transformed skin equivalents are applied to the patient. In that case, the agents which induce expression, if needed, can be given parenterally to the patient or applied topically to the skin equivalents.

The following examples further illustrate the invention.

EXAMPLE 1

GENERAL METHODS

Isolation of genomic clones of human TGase I. A human placental EMBL-3 SP6/T7 genomic library (Clontech, Palo Alto, Calif.) was screened by standard procedures with the human TGaseI cDNA (26) as a probe. The [$\alpha$-$^{32}$P]dCTP labeled 126a probe (11) was prepared using a random-priming method, purified on a Sephadex G-50 spun column and hybridized at high stringency (1M NaCl, 1% SDS, 150 µg/ml carrier DNA at 65° C.) to ten 150 $cm^2$ Gene Screen Plus filters containing a total of $3\times10^5$ plaques on *E. coli* LE392 strain. Phages from signal-positive plaques were purified to homogeneity, and the DNA was isolated by the glycerol gradient method (26). The insert DNA was released from the 11 positive clones by cleavage with XhoI restriction enzyme, size fractionated on an agarose gel and analyzed by Southern blot for sequence homology with the 126a cDNA.

Restriction enzyme mapping and Southern blots. A physical map of 3 isolated genomic clones (EMBL-B, EMBL-K, and EMBL-N) was constructed by single and double digestion of that DNA with restriction enzymes XhoI, SacI, EcoRI and BamHI (FIG. 1). The DNA restriction fragments and the control DNA markers were separated by gel electrophoresis for size estimation in kb. After transferring onto nylon filters, DNA fragments containing the 5' and 3' ends of the gene were identified by Southern blots and hybridized with the [$\gamma$-$^{32}$P]ATP end-radiolabeled oligonucleotide probes #219 (nucleotides 29–45 where nucleotide 1 corresponds to the first A in the first ATG codon of the cDNA) and. #220 (nucleotides 2343–2360). Filters were hybridized under low stringency (1M NaCl, 1% SDS, 150 ug/ml of carrier DNA at 37° C.). The oligonucleotides, whose sequences were designed based on the known TGase I cDNA sequence, were synthesized in the Department of Microbiology at the University of Rochester. The cleavage position of one enzyme with regard to another was defined by complete additivity of lengths of obtained DNA fragments, Southern blot analysis and the sequencing data. For genomic Southern blot analysis, high molecular weight genomic DNA extracted from human peripheral leukocytes was digested with several restriction endonucleases, and the DNA fragments were electrophoresed on a 0.8% agarose gel. After transferring onto filters, the genomic fragments were hybridized with the nick-translated $^{32}$P-labeled 126a (nucleotides 14–1652) and 16b (nucleotides 314–2622) cDNA probe and K3 and K5 genomic subclones containing 5'- and 3'-end sequences, respectively (see FIG. 2). Autoradiographs were exposed on Kodak X-ray films for 1–3 days.

Figure 2:
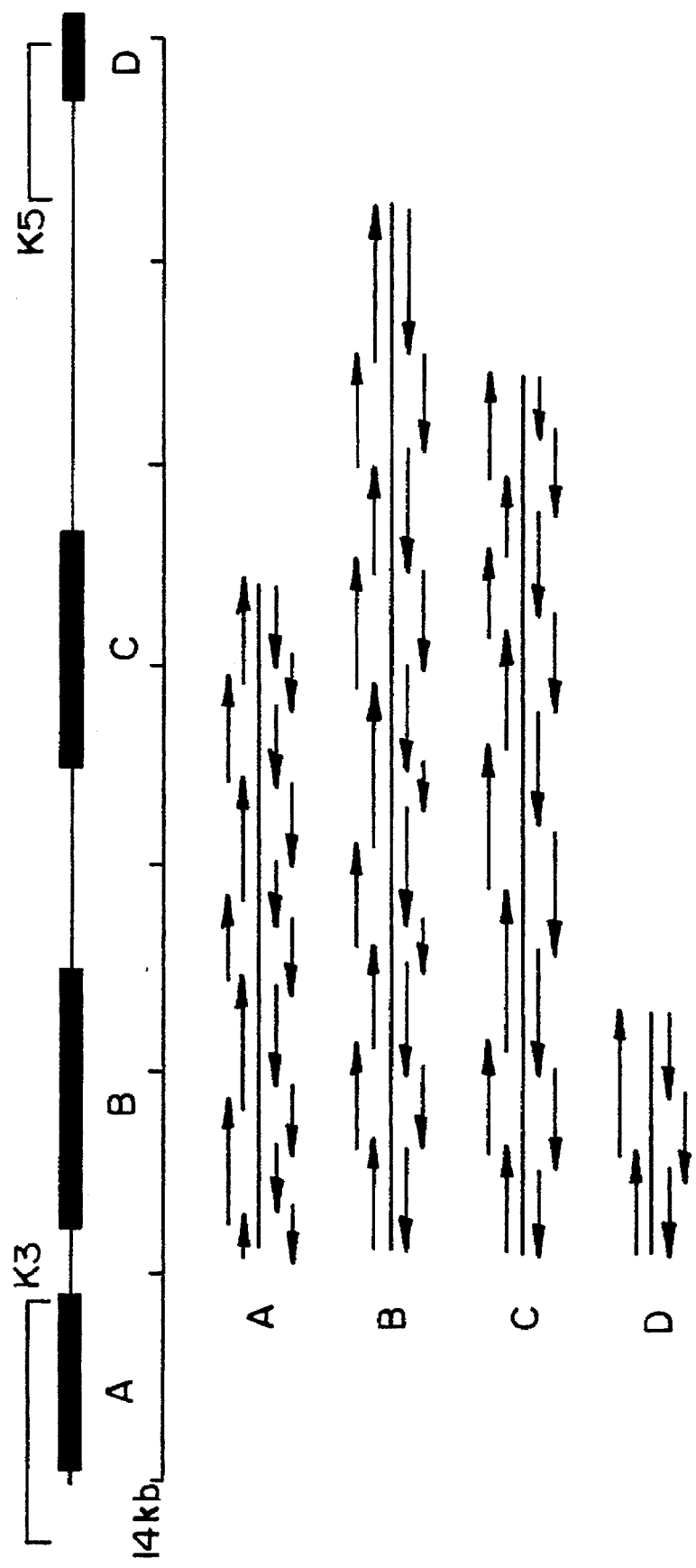
FIG. 2 depicts the regions of the genomic clones for the human TGase I gene which were sequenced together with the location of the K3 and K5 probes. The sequencing strategy for regions A–D are indicated in the lower portion of the figure.

Other DNA manipulations. Restrict enzyme digestions, ligations, enzymes for deletion analysis and other DNA analysis methods were conducted in accordance with manufacturers instructions or as described in Sambrook et al. (1989) *Molecular Cloning: A Laboratory Manual*, 2nd Ed., Cold Spring Harbor Laboratory Press, Cold Spring Harbor, N.Y. DNA sequencing. DNA sequence was determined using the Sequenase® kit and plasmid sequencing protocol (U.S. Biochemical Corp.). The strategy used included both subcloning into pUC19 or pUC18 vectors and synthetic oligonucleotide primer methods as illustrated in FIG. 2. In FIG. 2, the upper level illustrates sequenced parts (thick bars) and location of the K3 and K5 genomic subclones (brackets) in relation to the entire gene. The lower level is a detailed diagram of the sequenced regions designated as A, B, C and D, which correspond to GeneBank accession numbers: M83227, M83228, M83229 and M83230. Solid-headed arrows indicate direction of sequencing by synthetic oligonucleotide primers method and open-headed arrows indicate direction by the subcloning technique.

Cell Culture. Neonatal keratinocyte cultures of human foreskin were established and maintained as described by Rheinwald, J. G. et al. (1975) *Cell* 6:331–341 or by Haake et al. (1991). Other cells lines . . . (fibroblasts, established keratinocytes). Transfections were performed after the third passage of the human foreskin keratinocytes.

CAT Assay. CAT assays were performed according to the method described by Gorman et al. (1982) *Mol. Cell. Biol.* 2:1044–1051. Transfected cells were lysed in 0.25M Tris HCl (pH 7.5) by rapid freeze-thawing; cell debris was removed by centrifugation and the extract was either stored at −70° C. or used immediately for CAT assay. To 0.1 ml volume of extract from 5×10$^5$ cells, 63 μl of a mixture containing $^{14}$C-chloramphenicol (0.3 μCi/6.3 nmol) in 80 mM Tris-HCL (pH 7.5) was added followed by 10 μl of 40 mM acetyl CoA (Sigma). After 60 min of incubation at 37° C. the reaction was stopped by adding 1 ml of ice-cold ethyl acetate and vortexing. The reaction mixture was centrifuged and the upper phase removed, evaporated under vacuum, and resuspended in 10 μl of ethyl acetate. The final product was separated on thin-layer chromatography (TLC) plates (American Scientific Products) in chloroform:methanol (95:5), dried and auto-radiographed overnight.

EXAMPLE 2

CLONING OF THE GENOMIC HUMAN TGASE I GENE AND IDENTIFICATION OF ITS PROMOTER REGION

Isolation and characterization of the human TGase I gene.

About 3×10$^5$ recombinant phage plaques were screened from the human genomic library, and eleven contained DNA sequences that hybridized to the TGase I cDNA. The hybridization-positive phages were isolated, plaque-purified and their DNA was digested with several restriction enzymes. Three unique clones were identified: EMBL-B, EMBL-K and EMBL-N. The restriction map constructed for these 3 clones by single and double digestion with BamHI, SacI, XhoI and EcoRI revealed that the clones overlap, as shown for the BamHI map in FIG. 1. Southern blot analysis of the restricted fragments with the oligonucleotide probes homologous to the 5' and 3' ends of the cDNA, demonstrated that the EMBL-B, -K and -N clones covered the entire human TGase I gene whose transcription unit spans 14.2 kb of genomic DNA. The EMBL-B clone contains about 10 kb of the 5'-upstream region flanking the gene and about 4 kb overlap with the EMBL-K clone. The EMBL-K clone spans almost the entire transcription unit of the human TGase I gene. Nucleotide sequence analysis of the 5' and 3' ends of this clone established that it begins 930 bp upstream from the presumptive transcription start site and ends 86 bp after the TAG amber stop codon. The AATAAA polyadenylation signal is located 156 bp downstream from the termination code and therefore is not present in the EMBL-K clone.

The polyadenylation signal sequence is present, however, in the EMBL-N clone, which extends the EMBL-K clone for over 2.1 kb downstream from the stop codon. Thus, the entire human TGase I gene with its 5'- and 3'-flanking regions has been isolated. The authenticity of the human TGase I gene was verified by Southern blot analysis of digested genomic DNA from human leukocytes and from the cloned bacteriophage gene using 126a and 16b cDNA and genomic K3 and K5 subclones as probes. The K3 and K5 probes are shown in FIG. 2.

Approximately one half of the cloned gene was sequenced, including 6977 bp out of 14.2 kb of the TGase I transcription unit and 930 bp of the 5'-upstream flanking region. The sequenced regions and sequencing strategy are illustrated in FIG. 2. Comparison of the genomic sequence to that of the cDNA (the functional mRNA has been found to be 2630 bp long excluding the polyA tail) revealed the split character of the human TGase I gene. The gene is composed of 15 exons separated by the intervening sequences of 14 introns. Exon I and part of exon XV encode 5'- and 3'-untranslated regions, respectively, which by analogy to other eukaryotic genes may play an important post-transcriptional regulatory role.

The sequence of 86 bp of the 5'-untranslated region is divided by intron 1 between nucleotides 84 and 85. The remaining two nucleotides of the 5'-untranslated region are separated by a 734 bp long intron and precede the first AUG translational start codon located in the exon II. The size of exon I was estimated based on the primer extension analysis of the human TGase I mRNA reported by Kim et al., which is a few nucleotides longer than those reported by Phillips et al. and Yamanishi et al. The longer, 86 base primer-extended fragment is more likely, however, to contain the transcriptional initiation site, because the cytidine at which this fragment begins is located, as expected for a eukaryotic gene, 30 bp downstream from the CATAA sequence. This sequence is the only TATA-like sequence among the 930 bp analyzed 5'-upstream and appears to represent a functional but weak TATA box, an important sequence motif for promoter strength and mRNA start-site selection. A relatively weak TATA-box consensus sequence can cause initiation of mRNA transcription at multiple sites, which could explain the differences in the reported sizes for the TGase I primer-extended products.

EXAMPLE 3

DETERMINATION OF TRANSFECTION CONDITIONS a) Liposome-Mediated Transfection. To introduce DNA into keratinocytes or fibroblasts the lipid-mediated transfection protocol of Rose et al. (1991) *BioTechniques* 10:520–524, was followed. Liposomes were prepared with 5 mg/ml of cationic lipid dimethyldioctadecylammonium bromide (DDAB) and 1 mg/ml of neutral lipid dioleoyl-L-α- phosphatidylethanolamine (PtdEtn). Keratinocytes were grown in 60 mm culture dishes in keratinocyte growth medium (KGM) and fibroblasts in RPMI medium+10% fetal calf serum (FCS) until the cells reached 50–70% confluency. The night before transfection, cells were fed with their respective medium. The transfection mixture, 1.5 ml Dulbecco's Modified Eagle Medium (DMEM), 12 μg of DNA and 45 μl of the lipid mix, was incubated at room temperature for 10 min before addition to medium-washed cells for 4 h at 37° C. After 4 h an equal volume of KGM or RPMI supplemented with 4% FCS was added for an additional 2 h. The cells were then washed with growth medium and grown for 48 h in 3 ml of either KGM or RPMI medium with 2% FCS. After this time, the cells were harvested for CAT assay.

b) Polybrene Method. Cells were plated 24 h prior to transfection at the density of $10^5$ cells/ml. Polybrene (30 μg/ml) was added for 2 h directly to the culture dish. The growth medium was removed except for 0.5 ml to cover cells, and 10 μg of DNA was added for an additional 6 h. After 4 h of incubation, chloroquine was added to a final concentration of 100 μM for the remaining 2 h. The chloroquine step was often omitted because of a minimal effect on the transfection efficiency. Transfected cells were washed with growth medium and grown for 48 h in 3 ml of this medium supplemented with 2% serum. These cells were then harvested for CAT assay.

c) Results and Conclusions. The lipid-mediated transfection method is more efficient then the polybrene method in introducing exogenous DNA into keratinocytes. Keratinocyte growth is not noticeably affected by the lipid-mediated transfection, so it became the transfection method of choice.

EXAMPLE 4

DELETION ANALYSIS OF THE HUMAN TGASE I GENE PROMOTER REGION

A. Construction of deletion mutants.

To define cis-acting regulatory DNA sequences involved in controlling human TGase I gene expression, several chloramphenicol acetryltransferase (CAT) plasmids were constructed. Each deletion mutant construct contains different segments of the TGase I promoter region linked to the CAT gene.

Figure 4:
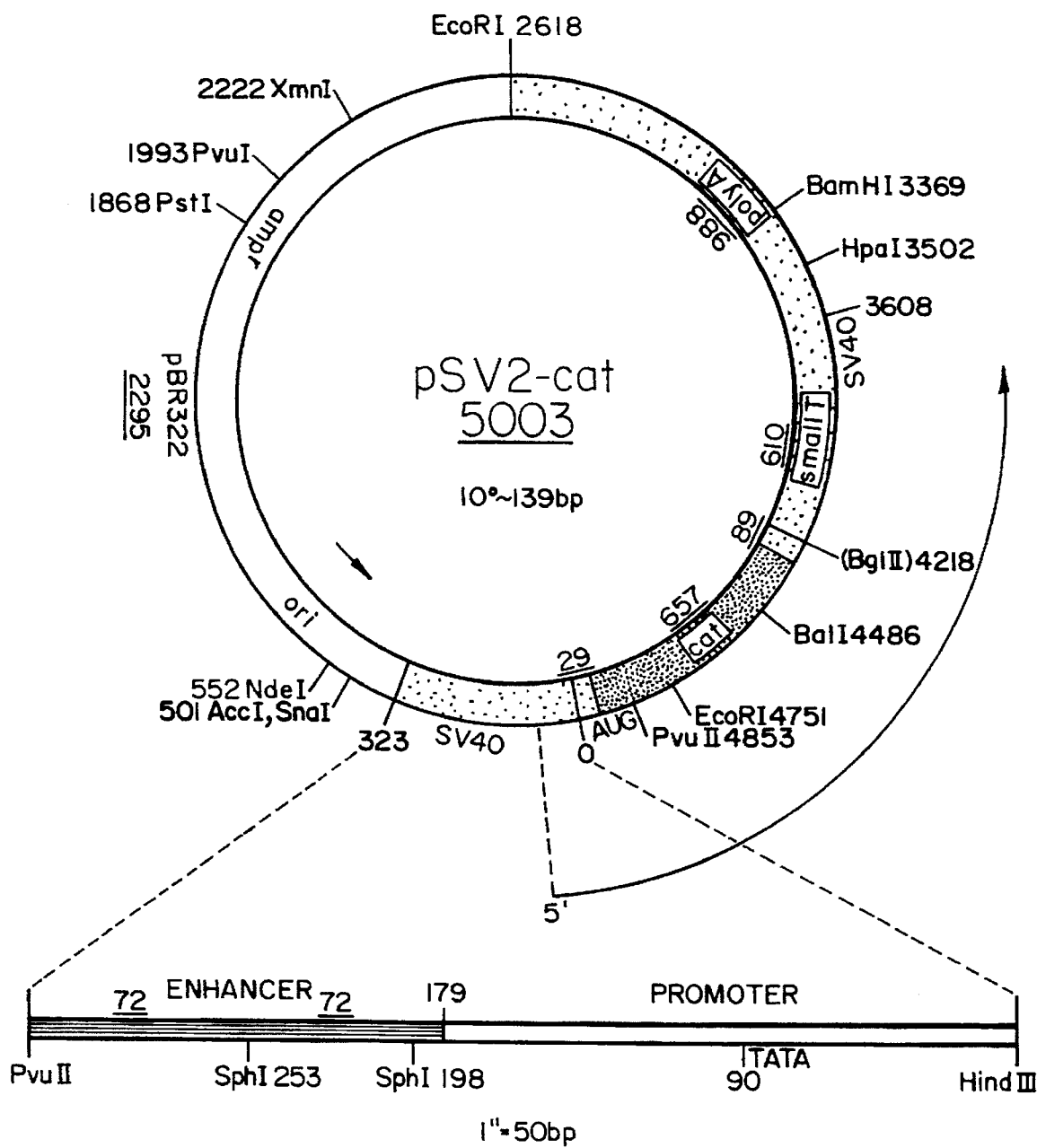
FIG. 4 depicts the plasmid pSV2-cat which contains the chloramphenicol acetyltransferase (CAT) gene under control of the SV40 promoter and enhancer elements. This plasmid served as a positive control for CAT expression.
Figure 5:
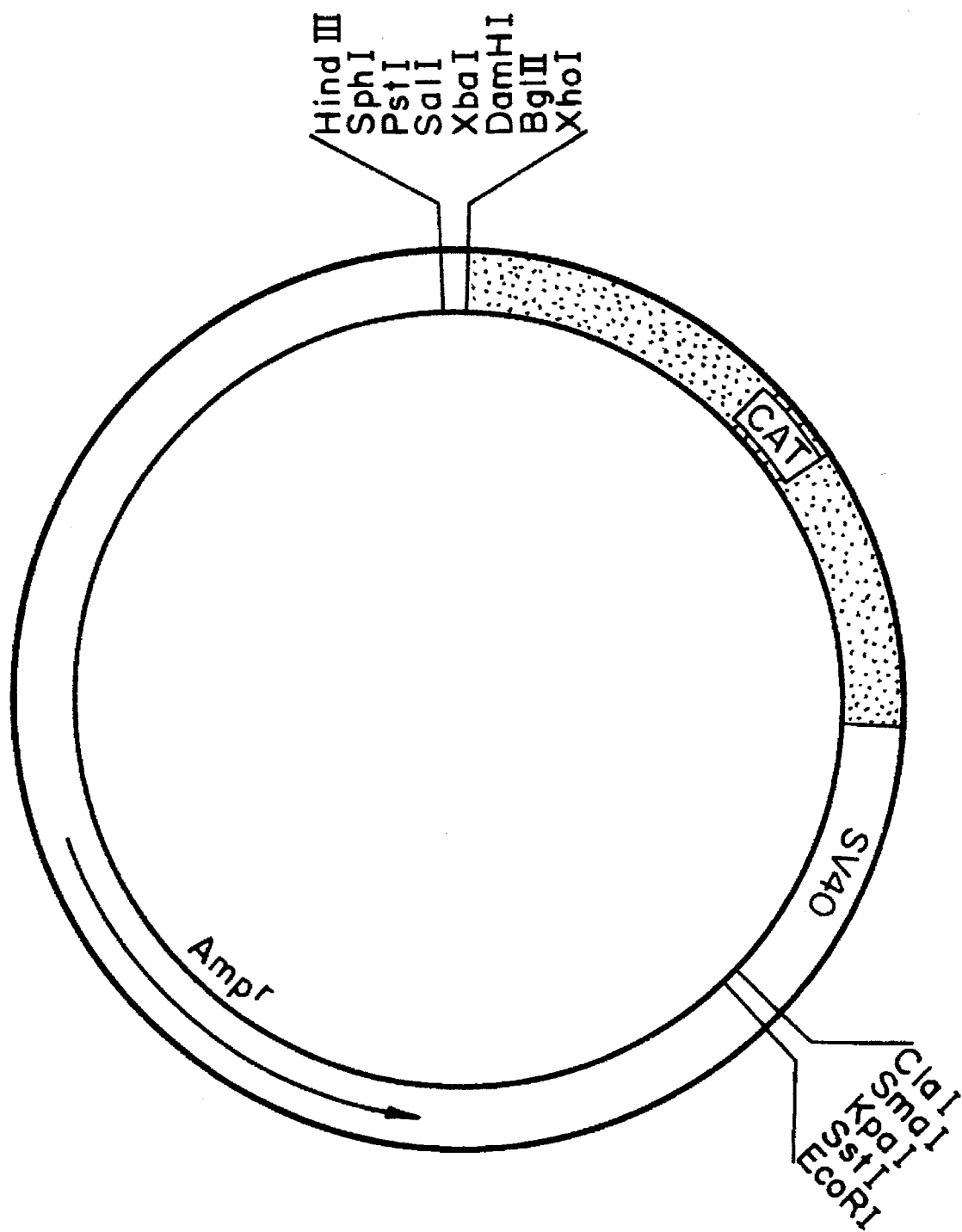
FIG. 5 depicts the plasmid pBLCAT-3 which is a modified version of pSV2-cat lacking the SV40 promoter and enhancer elements. This plasmid served as a negative control for CAT expression as well as the parent plasmid for the deletion mutants described in Example 4.

These constructs were made using plasmid pBLCAT-3 as the parent vector (FIG. 5). Plasmid pBLCAT-3 is similar to pSV2-cat except that it lacks the SV40 promoter and enhancer elements in the PvuII-HindIII fragment depicted in FIG. 4. The deletion mutant construct containing the BamHI fragment was made by inserting the BamHI fragment from the human TGase I promoter region (Table 1) into the BamHI site of the polylinker adjacent to the CAT gene start codon in pBLCAT-3. The construct containing the NlaIII-194 fragment was made by inserting the NlaIII-194 fragment from the human TGase I promoter region (Table 1) into the SphI site of the polylinker. The construct containing the HindIII fragment was made by inserting the HindIII fragment of the human TGase I promoter region into the HindIII site of the polylinker. The double mutant containing the NlaIII-194 fragment and the HindIII fragment (also called the 194+ fragment) was constructed by inserting the HindIII fragment into the plasmid containing the NlaIII-194 fragment after HindIII digestion of that plasmid.

B. Analysis

Figure 3:
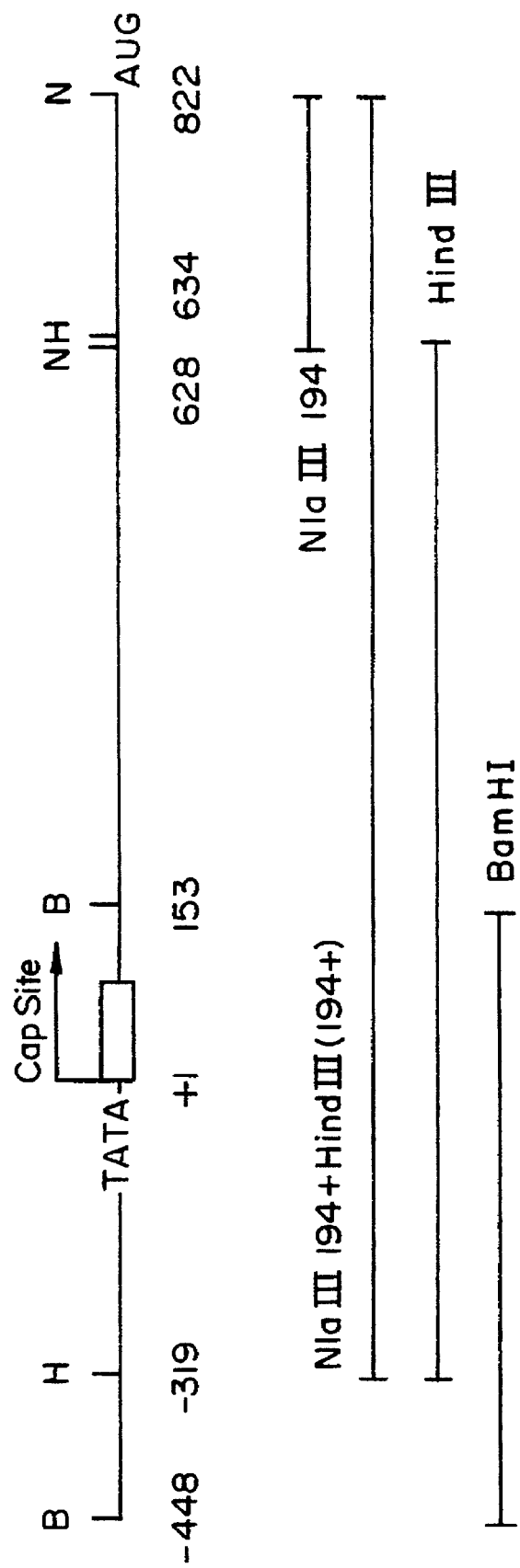
FIG. 3 depicts a restriction map of 1270 base pairs (bp) from the 5'-regulatory region of the human TGase I gene (upper half) and various mutants analyzed for promoter activity (lower half). For the mutants, the solid lines indicate the fragments of DNA present in the CAT constructs (see Examples for further details).

Analysis of the promoter region was undertaken with the 1270 bp DNA fragment located between nucleotides −448 and 822, in relation to the presumptive CAP site, upstream from the AUG translational start codon as numbered in FIG. 3. The deletion mutants NlaIII194, 194+, HindIII and BamHI (see map in FIG. 3) were assayed for CAT gene activity in transiently transfected primary neonatal keratinocytes grown in low (0.07 mM) $Ca^{+2}$ and in high (1.2 mM) $Ca^{+2}$ medium in the presence and absence of $10^{-6}$M retinoic acid (RA). Assays for CAT activity were conducted 48 or 72 h after transfection. When high $Ca^{2+}$ or RA was present, cells were transfected, cultured with $Ca^{2+}$ or RA for 72 h and then assayed. The activity of the pSV2-cat plasmid and of the pBLCAT3 vector served as positive and negative controls, respectively, for all TGase I promoter constructs.

The results of the deletion analysis of the human TGase I promoter are shown in Table 2. These data indicate that the −448 to 822 DNA fragment contains regulatory elements which control the rate of TGase I gene transcription. The NlaIII194 mutant, which contains 194 bp of the first intron immediately adjacent to the AUG codon, conferred the highest promoter activity. This activity was reduced two fold by high $Ca^{+2}$ but restored in keratinocytes treated with RA. Furthermore, addition of the HindIII DNA fragment in the 194+ mutant exhibited an inhibitory effect on CAT gene activity and eliminated responsiveness of the NlaIII194 DNA fragment to $CA^{2+}$ and RA. This result indicates a negative regulatory role for the HindIII sequences in controlling TGase I gene expression. The HindIII DNA fragment alone is unable to initiate transcription of the CAT gene although it encodes the untranslated exon I and 319 bp upstream from the transcription initiation CAP site including the TATA-like box. Interestingly, the TATA-like box appears to have promoter activity in the BamHI mutant. This result indicates that the DNA fragment defined by 3′ BamHI and HindIII sites in FIG. 3 (i.e. nucleotides 1088 and 1569 of SEQ ID NO:1) contains a negative regulatory element for the human TGase I promoter. Finally, the BamHI mutant contains a $Ca^{+2}$-responding element since its transcriptional activity is increased in cells grown in high $Ca^{+2}$ medium.

In summary, the data shows that TGase I gene expression can be regulated by two distinct DNA fragments both with transcription-promoting activities. The nucleotide sequences of these fragments contain positive and negative regulatory elements which control TGase I gene responsiveness to cellular and environmental factors.

TABLE 2

| CAT Assay for Regulatory Elements in the Human TGase I Gene Promoter Region | | | | | | | |
|---|---|---|---|---|---|---|---|
| Plasmid[a] | pSV2 | pBL3 | B | H | N | 194+ | None |
| Control[b] | 91.9 | 0.84 | 4.59 | 0.11 | 18.1 | 8.61 | 0.09 |
| Hi $Ca^{2+}$ | 86.5 | 0.37 | 8.37 | 0.11 | 8.12 | 6.25 | 0.10 |
| Hi $Ca^{2+}$ + RA | 80.1 | 0.69 | 4.47 | 0.10 | 19.4 | 7.63 | 0.09 |

[a]The indicated plasmids were transiently transfected into primary neonatal keratinocytes and assayed for CAT activity. Activity is expressed as percent acetylated. The plasmids are as follows: pSV2, pSV2-cat (positive control); pBL3, pBLCAT-3 (negative control); B, BamHI fragment in pBLCAT-3; H, HindIII fragment in pBLCAT-3; N, NlaIII-194 fragment in pBLCAT-3; 194+, HindIII-NlaIII-194 fragment in pBLCAT-3; None, no DNA.
[b]Control is low calcium (0.07 mM $Ca^{2+}$); Hi $Ca^{2+}$ is 1.2 mM $Ca^{2+}$; Hi $Ca^{2+}$ + RA is 1.2 mM $Ca^{2+}$ and $10^{-6}$ M retinoic acid.

We claim:

1. An isolated DNA comprising a transcriptional regulatory region from a human type I transglutaminase gene wherein said DNA comprises a BamHI restriction fragment consisting of the nucleotide sequence of bases 485 to 1093 of SEQ ID NO:1.

2. An isolated DNA comprising a transcriptional regulatory region from a human type I transglutaminase gene wherein said DNA comprises an NlaIII restriction fragment consisting of the nucleotide sequence of bases 1563 to 1760 of SEQ ID NO:1.

3. An isolated DNA comprising a transcriptional regulatory region from a human type I transglutaminase gene wherein said DNA comprises an HindIII restriction fragment consisting of the nucleotide sequence of bases 616 to 1574 of SEQ ID NO:1.

4. An isolated DNA comprising a transcriptional regulatory region from a human type I transglutaminase gene wherein said DNA comprises an HindIII-NlaIII restriction fragment consisting of the nucleotide sequence of bases 616 to 1760 of SEQ ID NO:1.

5. An isolated DNA comprising a transcriptional regulatory region from a human type I transglutaminase gene wherein said DNA comprises a BamHI restriction fragment consisting of the nucleotide sequence of bases 485 to 1093 of SEQ ID NO:1, wherein said fragment comprises a polynucleotide sequence encoding a keratinocyte-specific regulatory element and a calcium-responding regulatory element.

6. An isolated DNA comprising a transcriptional regulatory region from a human type I transglutaminase gene wherein said DNA comprises an NlaIII restriction fragment consisting of the nucleotide sequence of bases 1563 to 1760 of SEQ ID NO:1, wherein said fragment comprises a polynucleotide sequence encoding a keratinocyte-specific regulatory element, a calcium-responding regulatory element and a retinoic acid-responding regulatory element.

7. An isolated DNA comprising a transcriptional regulatory region from a human type I transglutaminase gene wherein said DNA comprises an HindIII restriction fragment consisting of the nucleotide sequence of bases 616 to 1574 of SEQ ID NO:1, wherein said fragment comprises a polynucleotide sequence encoding a negative regulatory element which inhibits calcium and retinoic acid responsiveness.

8. An isolated DNA comprising a transcriptional regulatory region from a human type I transglutaminase gene wherein said DNA comprises an HindIII-NlaIII restriction fragment consisting of the nucleotide sequence of bases 616 to 1760 of SEQ ID NO:1, wherein said fragment comprises a polynucleotide sequence encoding a keratinocyte-specific regulatory element, a calcium-responding regulatory element and a retinoic acid-responding regulatory element.

9. An isolated DNA comprising a transcriptional regulatory region from a human type I transglutaminase gene wherein said sequence comprises nucleotides 1 to 1757 of SEQ ID NO:1.

10. A replicable expression vector comprising the DNA of any one of claims 5 or 9 wherein said DNA is operably linked to the coding sequence of a gene product and is thereby capable of effecting expression of said gene product of interest.

11. The vector of claim 10 wherein said gene product is a human type I transglutaminase, a marker gene, or a heterologous gene product of interest.

12. The vector of claim 11 wherein said marker gene is chloramphenicol acetyl transferase, β-glucuronidase, or β-galactosidase.

13. The vector of claim 11 wherein said heterologous gene product is a keratin, an acidic keratin, a basic keratin, an enzyme, an interferon, an interleukin, GM-CSF, G-CSF, M-CSF, a retinoic acid receptor, a steroid hormone receptor, a vitamin D receptor, epidermolysin, filaggrin, loricrin, cystic fibrosis transmembrane receptor, growth hormone, insulin, parathyroid hormone, ACTH, substance P or an endogenous opiate.

14. A host cell comprising the expression vector of claim 10.

15. The host cell of claim 14 wherein said host is a bacterium, a yeast cell or a mammalian cell.

16. The host cell of claim 15 wherein said mammalian cell is a human keratinocyte.

17. A method for keratinocyte-specific expression of a gene product of interest which comprises cultivating a keratinocyte cell which comprises any one of the expression vectors of claims 10–13, for a time and under conditions effective to express said gene product of interest.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 2003 base pairs
( B ) TYPE: nucleic acid
( C ) STRANDEDNESS: both
( D ) TOPOLOGY: linear ( i i ) MOLECULE TYPE: DNA (genomic)

( x i ) SEQUENCE DESCRIPTION: SEQ ID NO:1:

```
GAGCTCGAGG ATCGCCTTGG TGCCATCCTC AGTGTTTCCC CAGTGTCGGG GTGGAGTAAG      60
GATGCACACA GCACAGGTGC CTGAGCCGGT TGGTCTGGAT TCCCAGGAAG AATTCCAGGT     120
TGGAGAAAAG GGAATCCTCT AGTCCAGCTG AGCAGAGACT CCTCTCAGTG AGAGAAAGGT     180
ACTCTGTACC CCTGGAAGGG ACTCAGTTCC CACCCAAGCC TGAGTGGAAA GGCTAAACA      240
TCCCCTAACC CCCGAGGCTA CAGCGGGGGT GGGGACGTG  AAATGAGATT GCTCCTACTC     300
TGATCTCCCT AATCCCAAAC TTGAGGGCAG CTCACTCATG CCTGGGGCTG TAGAGCAGCT     360
GAGAAAGAAG GGACAGACTT GGGGGTGGAG GGAGTCAGAA TATCTGGTAG AGCCAGCAGG     420
TCAGGGGTTA GCTGGTGGAG CCAGTCTGAG GGCCTGGCTG CTGATGTCAC CAGTCTGCAA     480
CCTGGGATCC CAGGACCTCC CTGGGCAGGA TGAGTTCCAG GACCAGGCCC CTGGGCCAAT     540
TTCATAGGGC TGAGCCTGGC TTGGGCTGCA CAGAACTCGG CAGCAGGAGC CTGTGACAGC     600
AGAGGTAGGC AGCCTAAGCT TGGGACCAGA AGGTCGGCCA GACAGGGCTG TGGGTGGAAG     660
GGCCTGCCTG CCCCACTGCC CTTGCAGCTT CTTCATCCGG GAGAAGGGGC TCCTCACATG     720
CCCAGTCTGG TAGGAATCAG CCTGGTGCCA GGGGCCATCA CAGCGGTGGC TCCCACCAAA     780
GCCCAGCCTA AGCCCCAGA  CCTCACCCCT GCTCCCTCCC TAGCATCTTC TCCCCATTTC     840
CCGCCCAGAG GCCTGGCCTC TTCTCTCCGC CCCCTACAGC AGTTTGGCCC CTCCCTCCCA     900
CATAAGTCAC TTACCAGGTC TGTCCCTGCG GCATCCAGTC TGTGGGTCCT GTCCATCCA      960
TCCTGACCTG TTCCATCTCA GCCCCAGGAC TCAGTACTGC GGTTGCCAAC ACTGCTGCCA    1020
GGTGAGGGGC TCCCACGGGT ACTGTGGTGC CGAGTCCAGG CGGCCCACAC TATCAGAGGC    1080
CGTGCCTGGA TCCAGCAAGG TGGGGTGTGG GCCAGCTGTG TACCTGTCAG CCCCAGCTAG    1140
GCTGTTCCCA ACACCAAGAC TCTGCTTTCC CTGTGCACAG GCTCCGGGCA CCTGCCATGC    1200
CCTACCCCTC CTGGCAGCCC CAAGTGGGGT CTTCCCTGAC TTGGGAATGC CAAGGACCAC    1260
AGGCCCCGGG GTCACTTGTC TGTCTTGTGA GGAACCTTGA GTTGGGGAT  TTCTGCTAAG    1320
AAATGAGTTC TAGAAGCTGT CAGTGTTGTG CACCTCTAGA CTGCAGAGCT AGCAGGTGGA    1380
CGGACCAGGC CCAGGGATGC TGGAGCACTC TGATGTGTGT GCAGCTGGGT CTTGAGGCTG    1440
GGACAAGTGT CCATGCAGGG AACTATGTGG ATTTCCTGGG ATGGATCGTT GAGTGGGTTT    1500
CTTCATTGGG CAGTTTTTCG GATGTTGTTT GGTGGGGGTG AGGGAAGGC  TTTTCTCTGC    1560
AGCATGAGAA GCTTCTCTGG GTGAGTCTGA ATGGTCTTCG CGGAAGGTCT CTGGATGTGT    1620
CTGGAGAATC TCTGGGCCAA GGTGGGATTG TTTCGGTCAT CGGGTGGGAC TGAATCAGCT    1680
GTCTGGATGG AGGGTTTCTG GGTCAACTGG CTGGACTAC  CTGGGTTAAG GAGCCACCCT    1740
GCCTCTTCCT AACAGGCATG ATGGATGGGC CACGTTCCGA TGTGGGCCGT TGGGGTGGCA    1800
```

| | | | | | | |
|---|---|---|---|---|---|---|
| ACCCCTTGCA | GCCCCCTACC | ACGCCATCTC | CAGAGCCAGA | GCCAGAGCCA | GACGGACGCT | 1860 |
| CTCGCAGAGG | AGGAGGCCGT | TCCTTCTGGG | CTCGCTGCTG | TGGCTGCTGT | TCATGCCGAA | 1920 |
| ATGCGGCAGA | TGACGACTGG | GGACCTGAAC | CCTCTGACTC | CAGGGGTCGA | GGGTCCAGCT | 1980 |
| CTGGCACTCG | AAGACCTGGC | TCC | | | | 2003 |